(12) United States Patent
Li

(10) Patent No.: US 11,578,134 B2
(45) Date of Patent: Feb. 14, 2023

(54) HUMAN BLADDER CANCER MARKER AG-CD71 AND ANTIBODY ABC71 AND APPLICATION THEREOF

(71) Applicant: Chong Li, Beijing (CN)

(72) Inventor: Chong Li, Beijing (CN)

( * ) Notice: Subject to any disclaimer, the term of this patent is extended or adjusted under 35 U.S.C. 154(b) by 301 days.

(21) Appl. No.: 16/639,111

(22) PCT Filed: May 30, 2018

(86) PCT No.: PCT/CN2018/089037
§ 371 (c)(1),
(2) Date: Feb. 13, 2020

(87) PCT Pub. No.: WO2019/033824
PCT Pub. Date: Feb. 21, 2019

(65) Prior Publication Data
US 2020/0207863 A1    Jul. 2, 2020

(30) Foreign Application Priority Data

Aug. 14, 2017    (CN) .......................... 201710692872.2

(51) Int. Cl.
| | | |
|---|---|---|
| *C07K 16/28* | (2006.01) | |
| *A61K 47/68* | (2017.01) | |
| *A61P 35/00* | (2006.01) | |
| *C07K 16/30* | (2006.01) | |
| *G01N 33/574* | (2006.01) | |
| *A61K 38/00* | (2006.01) | |
| *A61K 39/00* | (2006.01) | |

(52) U.S. Cl.
CPC .......... *C07K 16/2881* (2013.01); *A61K 47/68* (2017.08); *A61P 35/00* (2018.01); *C07K 16/30* (2013.01); *G01N 33/574* (2013.01); *A61K 38/00* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 4,208,479 A * | 6/1980 | Zuk | C07J 41/0016 436/826 |
| 6,933,142 B1 * | 8/2005 | Bistrup | A61P 37/06 435/193 |
| 2007/0196874 A1 * | 8/2007 | Kannagi | G01N 33/57419 435/7.23 |
| 2013/0164216 A1 * | 6/2013 | Li | C12N 15/1137 424/1.49 |

OTHER PUBLICATIONS

Almagro & Fransson, Frontiers in Bioscience 2008; 13:1619-33 (Year: 2008).*

* cited by examiner

*Primary Examiner* — Peter J Reddig
(74) *Attorney, Agent, or Firm* — Bayramoglu Law Offices LLC

(57) ABSTRACT

A novel human bladder cancer marker AG-CD71 and a monoclonal antibody ABC71 for preventing AG-CD71 are provided. The human bladder cancer marker AG-CD71 is an abnormal glycosylated transferrin receptor TFRC; the abnormal glycosylated transferrin receptor TFRC refers to the TFRC carrying a saccharide structure Fucal-4 (GlcNAcbl-3)[6OSO3]GlcNAc as an epitope. Also provided is an antibody for the human bladder cancer marker AG-CD71; the antibody is the monoclonal antibody ABC71 specific for the human bladder cancer AG-CD71; the monoclonal antibody is secreted from the hybridoma cell strain the preservation number of which is CGMCC No. 14312.

7 Claims, 2 Drawing Sheets
Specification includes a Sequence Listing.

HUMAN BLADDER CANCER MARKER AG-CD71 AND ANTIBODY ABC71 AND APPLICATION THEREOF

CROSS REFERENCE TO THE RELATED APPLICATIONS

This application is the national phase entry of International Application No. PCT/CN2018/089037, filed on May 30, 2018, which is based upon and claims priority to Chinese Patent Application No. 201710692872.2, filed on Aug. 14, 2017, the entire contents of which are incorporated herein by reference.

TECHNICAL FIELD

The present invention mainly belongs to the technical field of tumor immunology, and particularly relates to a novel human bladder cancer marker AG-CD71 and a monoclonal antibody ABC71 for preventing AG-CD71. Cell and histology levels show that the ABC71 is capable of specifically recognizing human bladder cancer cells and human bladder cancer tissue. The present invention also relates to a method for detecting human bladder cancer by immunocytochemistry. The antigen detected by the detection method is the novel human bladder cancer marker AG-CD71 in the present invention, and the detection antibody is the monoclonal antibody ABC71 for preventing the human bladder cancer AG-CD71 in the present invention.

BACKGROUND

Bladder cancer is a malignant tumor on bladder mucosa, and is the most common malignant tumor, which also is one of ten common tumors. In China, its incidence rate ranks first in terms of urogenital neoplasms, but in western countries, its incidence rate ranks only second to prostate cancer. In China, as aging of population is aggravating, the smoking population is increasing, and industrialization process and environmental pollution are exacerbating, the incidence rate of bladder cancer is increasing year by year, and the overall incidence rate is in the 6th place among men, which ranks first in terms of urogenital neoplasms; wherein the incidence rate among men is 4 times of that among women, and the incidence rate increases with age. It is a serious damage to the health of population in China.

At present, the diagnosis and follow-up mainly depend on urethrocystoscopy. However, invasive urethrocystoscopy is expensive and inconvenient, it not only greatly painful for patients, but also has the risks of infection and bleeding etc. Urine is an ideal source of tumor markers. It is very necessary to find an efficient, simple and convenient, rapid, and sensitive diagnostic method for detecting bladder cancer by urine.

Transferrin receptor TFRC is a transmembrane glycoprotein on the surface of cells, of which the molecular weight is approximate 180 kD, and is consisted of two homologous dimer subunits crossed by two disulfide bonds. TFRC participates in iron absorption and cell growth regulation, and is an important medium for normal iron metabolism of human body. It has a low expression in all normal karyocytes, and has a relatively high expression level in cells with a high proliferation rate. Its expression is increased more significant especially in tumor cells possibly due to their requirement for iron. In recent years, TFRC gradually becomes a hot spot in basic and clinical researches and of tumor diseases.

Therefore, based on that the abnormal glycosylation of TFRC can change the malignancy of tumor cells, investigating the abnormal glycosylation of TFRC in bladder cancer provides a novel target for the screening, diagnosis, prognosis estimation and treatment of bladder cancer, and is very important for the diagnosis and treatment of bladder cancer.

SUMMARY

In the present invention, total protein extracted from fresh human bladder cancer tissue is used for immunizing mice, so a hybridoma cell strain is prepared. An antibody ABC71 capable of specifically binding to human bladder cancer tissue is screened out by ELISA method, which belongs to IgG1 subtype. Immunohistochemistry demonstrates that ABC71 antibody has an intense positive reaction with human bladder cancer tissue, but has no cross reaction with normal human bladder tissue.

In the present invention, it is identified by immunoprecipitation in combination with the results of mass spectrum and carbohydrate chip that antigen recognized by the ABC71 antibody is an abnormal glycosylated TFRC, which is localized on the cell membrane and has the epitope Fucal-4(GlcNAcbl-3)[6OSO3]GlcNAc, so it is an entirely novel human bladder cancer marker.

In the present invention, ABC71 antibody is coupled to horseradish peroxidase (HRP) to prepare horseradish peroxidase labelled anti-bladder cancer antibody (ABC71-HRP). After being bound to exfoliated bladder cancer cells in urine, it is developed by DAB. The smear is stained by hematoxylin, and then is detected under microscope. The kit is suitable for the early screening, prognosis monitoring, and auxiliary pathologic diagnosis of patients with bladder cancer.

The Technical Solutions of the Present Invention

Provided in the present invention is an entirely novel human bladder cancer marker-abnormal glycosylated transferrin receptor TFRC, which is designated as AG-CD71. Furthermore, also obtained is a hybridoma cell strain for producing an anti-AG-CD71 monoclonal antibody, which secretes monoclonal antibody ABC71, wherein the epitope recognized by the monoclonal antibody ABC71 is Fucal-4(GlcNAcbl-3)[6OSO3]GlcNAc. The monoclonal antibody has an intense positive reaction with human bladder cancer tissue, but has no cross reaction with normal human bladder tissue. Also provided in the present invention is an immunocytochemical diagnostic method of exfoliated cells in urine based on the monoclonal antibody ABC71.

Specifically, provided in the present invention is an abnormal glycosylated human bladder cancer marker AG-CD71, which is abnormal glycosylated transferrin receptor TFRC, wherein the saccharide structure containing the epitope on TFRC is Fucal-4(GlcNAcbl-3)[6OSO3]GlcNAc.

In a preferred embodiment, the amino acid sequence of the TFRC is shown by SEQ ID No: 1.

Another objective of the present invention is to provide an antibody for human bladder cancer marker AG-CD71, which is capable of specifically recognizing the saccharide structure Fucal-4(GlcNAcbl-3)[6OSO3]GlcNAc as the epitope, and the antibody is a polyclonal antibody or monoclonal antibody, preferably a monoclonal antibody.

Another objective of the present invention is to provide a kit for detecting human bladder cancer comprising the above-mentioned antibody ABC71 of the present invention.

In one preferred embodiment, the antibody is the monoclonal antibody ABC71 for human bladder cancer AG-CD71, which is secreted from hybridoma cell strain with the preservation number CGMCC No. 14312.

Another objective of the present invention is to provide a conjugate comprising the anti-human bladder cancer AG-CD71 antibody conjugated with a substance consisting of a component selected from a biomarker, antitumor drug, toxin and radioactive active agent.

Another objective of the present invention is to provide a kit for detecting human bladder cancer comprising the above-mentioned antibody of the present invention.

In one preferred embodiment, in the kit, the detection is performed by the monoclonal antibody ABC71 coupled to horseradish peroxidase, preferably, the ABC71 antibody is coupled to horseradish peroxidase to prepare a kit for detecting exfoliated cells in urine of bladder cancer. In one preferred embodiment, the sample to be detected contains exfoliated cells in urine of human bladder cancer.

Another objective of the present invention is to provide a hybridoma cell strain for secreting anti-human bladder cancer AG-CD71 monoclonal antibody ABC71 with the preservation number CGMCC No. 14312.

The Beneficial Technical Effects of the Present Invention are as Follows (1) an anti-human bladder cancer monoclonal antibody ABC71 is screened and prepared, which has an intense positive reaction with human bladder cancer tissue and has a negative reaction with normal human bladder tissue; (2) the epitope recognized by the ABC71 monoclonal antibody is found and identified, which is Fucal-4(GlcNAcbl-3)[6OSO3]GlcNAc, and is an entirely novel bladder cancer marker; (3) an high sensitive immunocytochemical method for detecting human bladder cancer based on ABC71 antibody is developed.

DETAILED DESCRIPTION OF THE EMBODIMENTS

Figure 1:
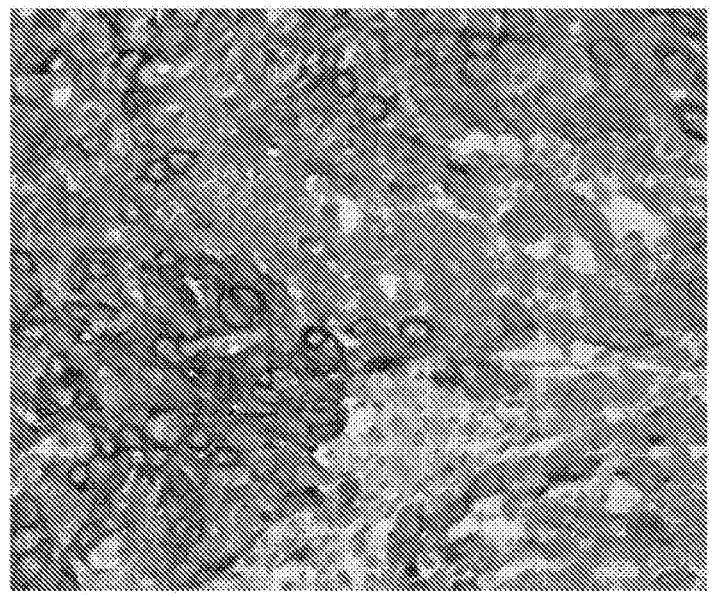
FIG. 1 is the immunohistochemical staining of human bladder cancer tissue slice by ABC71 monoclonal antibody (positive reaction)

In order to make the purposes, technical solutions and advantages of the present invention clearer, the present invention is further illustrated in detail below in conjunction with the accompanying drawings and embodiments. It should be understood that the specific embodiments described herein are merely used to explain the present invention, but not intended to limit the present invention.

In contrast, the present invention encompasses any replacement, modification, equivalent method and solution in the essence and scope defined by the claims. Furthermore, in order to make the public to understand the present invention better, in the following detailed description of the present invention, it describes some specific detail sections in detail. Those skilled in the art can fully understand the present invention without the description of these detail sections.

Embodiment 1

Preparation and Purification of ABC71 Monoclonal Antibody:

(1) Preparation of Hybridoma Cells 1) animal immunization and cell culture: total protein was extracted from human bladder cancer tissue after homogenization, then Balb/C mice (purchased from BEIJING VITAL RIVER LABORATORY ANIMAL TECHNOLOGY CO., LTD.) were intraperitoneally immunized with the total protein at the dose of 50 ug per mouse. The mice were immunized once again after two weeks. After the serum titer of the mice achieved the requirement, one booster immunization was performed on the mice. 3 days latter, spleens were removed from the mice and a splenic cell suspension was prepared thereby for cell fusion. Mouse myeloma cells Sp2/0 (ATCC CRL-1772) were thawed and screened with 8-AG (8-azaguanine) to maintain the sensibility of cells for HAT.

2) cell fusion: the splenic cell suspension prepared in step 1) was fused with the myeloma cells, for the specific method, reference can be made to Short Protocols in Immunology ((U.S.) J. E. Coligan, (U.S.) D. H. Marglics et al., Science Press, published in January 2009). The fused cell suspension was added into the culture medium containing cultured cells for culture. 24 hours latter, HAT selective medium (purchased from SIGMA COMPANY; HAT means: H: Hypoxanthine, A: Aminopterin, and T: Thymidine) was added for selective culture.

3) antibody detection: the hybridoma cell strain secreting the antibody was determined by ELISA method. The specific method was: total protein was extracted from bladder cancer tissue. The total protein was coated with 0.05 mol/L carbonate buffer (pH 9.6) at 4° C. overnight, then was blocked by 5% bovine serum albumin (BSA) at 37° C. for 3 hours. The mixture was washed with PBST 3 times, 100 ul supernatant to be detected was added therein, then was incubated at 37° C. for 1 h. The mixture was washed 3 times, horseradish peroxidase labelled anti-mouse secondary antibody IgG-HRP (purchased from BEIJING COMWIN BIOTECH CO., LTD.) was added therein, then was incubated at 37° C. for 1 h. The mixture was washed 3 times, 50 ul TMB (purchased from BEIJING ZHONG SHAN-GOLDEN BRIDGE BIOLOGICAL TECHNOLOGY CO., LTD.) was added for development. 5 min latter, 50 ul stop buffer was added. OD value was read at the wavelength 450 nm by a microplate reader. The OD value above twice that of negative control was considered as positive.

4) colonization and cryopreservation of hybridoma a colonized culture was performed on the screened positive hybridoma cells by using limiting dilution. After 5 cycles of colonized cultures, an expanded culture was performed on the hybridoma cells from which high titer monoclonal antibody was screened out.

A hybridoma cell strain obtained in the present invention was anti-human bladder cancer monoclonal hybridoma cell strain, which was deposited in China General Microbiological Culture Collection Center (CGMCC, Address: Institute of MicrobiologyChinese Academy of Sciences, NO. 1 West Beichen Road Chaoyang District Beijing China) on 27 Jul. 2017, and the preservation number was CGMCC No. 14312, the deposit was made under the Budapest Treaty.

(2) Preparation and Purification of ABC71 Monoclonal Antibody an expanded culture was performed on the hybridoma cell strain secreting the monoclonal antibody ABC71 (preservation number CGMCC No. 14312), and cell culture supernatant was collected. Affinity chromatography purification was performed on the monoclonal antibody ABC71 by using Protein G. The steps were: firstly, the Protein G affinity chromatography column (purchased from GE COMPANY) was equilibrated by phosphate buffer PBS; secondly, the cell culture supernatant containing the monoclonal antibody ABC71 passed through the Protein G affinity chromatography column; then, the chromatography column was washed by PBS until the OD value of the washing liquid from the column closed to 0; the Protein G affinity chromatography column was eluted by 0.2 mol/L glycine-HCL solution (PH 2.8), the eluant was collected, and the OD value was determined. The eluant containing the ABC71 monoclonal antibody was dialysed by PBS, then was cryopreserved at −20° C.

Embodiment 2

Figure 2:
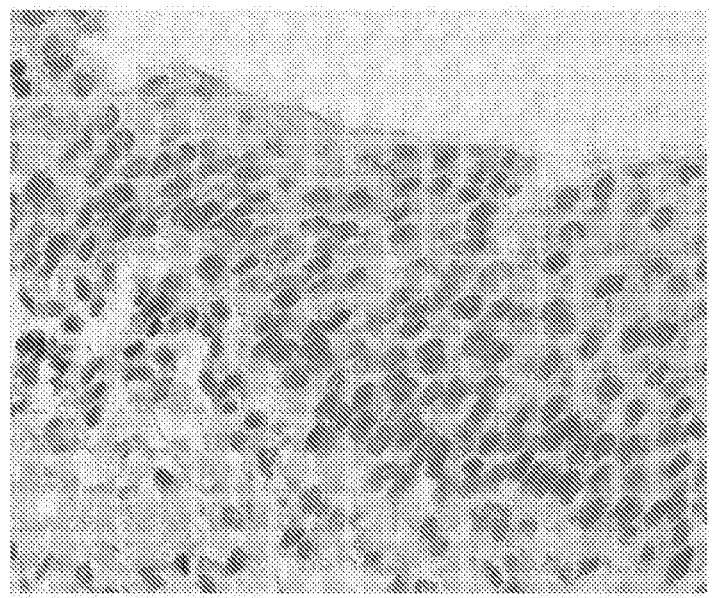
FIG. 2 is the immunohistochemical staining of normal human bladder cancer tissue slice by ABC71 monoclonal antibody (negative reaction)

Identification of ABC71 Monoclonal Antibody:

Immunohistochemistry was performed on human bladder cancer tissue and normal human bladder tissue slices by the ABC71 monoclonal antibody prepared in Embodiment 1, the results were shown in FIGS. 1 and 2. The results showed that human bladder cancer tissue presented a positive reaction by immunohistochemical staining of the ABC71 monoclonal antibody (as shown in FIG. 1), and normal human bladder tissue presented a negative reaction by immunohistochemical staining of the ABC71 monoclonal antibody (as shown in FIG. 2).

Human bladder cancer tissue and normal human bladder tissue were detected by using the ABC71 monoclonal antibody prepared in Embodiment 1 via immunohistochemistry, and the results were shown in table 1. The results showed that the ABC71 antibody has an intense positive reaction with human bladder cancer tissue, but has no cross reaction with normal human bladder tissue.

TABLE 1

Detection of immune reaction of anti-human bladder cancer monoclonal antibody ABC71 on human bladder cancer tissue and normal bladder tissue by immunohistochemistry

| Tissue (cancer tissue and normal tissue) | ABC71 antibody |
| --- | --- |
| Human bladder cancer tissue (patient #1) | Intensely positive (+++) |
| Normal human bladder tissue (patient #1) | Negative (−) |
| Human bladder cancer tissue (patient #2) | Intensely positive (+++) |
| Normal human bladder tissue (patient #2) | Negative (−) |
| Human bladder cancer tissue (patient #3) | Intensely positive (+++) |
| Normal human bladder tissue (patient #3) | Negative (−) |
| Human bladder cancer tissue (patient #4) | Positive (++) |
| Normal human bladder tissue (patient #4) | Negative (−) |
| Human bladder cancer tissue (patient #5) | Intensely positive (+++) |
| Normal human bladder tissue (patient #5) | Negative (−) |

Embodiment 3

Preparation of AG-CD71 Antigen:

1) total protein extraction: 100 mg human bladder cancer tissue was ground into a homogenate, 2 ml tris-detergent-containing lysis buffer was added, then was lysed at 4° C. for 10 minutes, then the lysate was centrifuged at 12,000 rpm for 20 minutes, the supernatant was taken, and it was total protein of human bladder cancer tissue.

2) immunoprecipitation: 50 ug ABC71 monoclonal antibody was added, then was incubated at 4° C. for 2 h.

Figure 3:
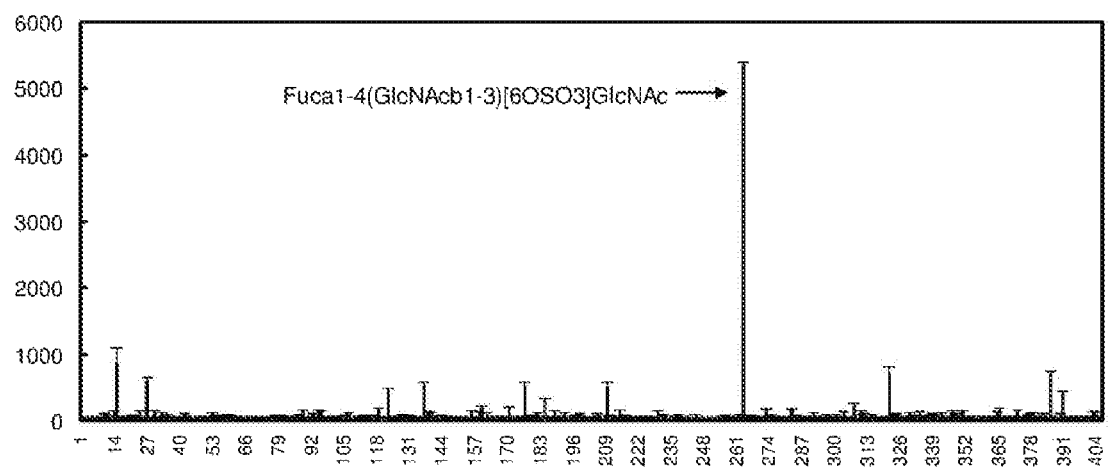
FIG. 3 is the detection result of carbohydrate chip.

3) antigen identification: 50 ul Protein G beads were added, then was incubated at 4° C. for 2 h. The beads were washed by PBS, then the beads were eluted by 0.2 mol/L glycine-HCL solution (PH 2.8) for mass spectrographic analysis. The result of the mass spectrometry was shown in table 2. The result of the mass spectrometry showed that the antigen of ABC71 was transferrin receptor TFRC. The carbohydrate chip data of the ABC71 monoclonal antibody was analyzed (as shown in FIG. 3), it was found that the epitope recognized by the ABC71 monoclonal antibody was the carbohydrate chain of TFRC, and the epitope was Fucα1-4(GlcNAcb1-3)[6OSO3]GlcNAc. Since the ABC71 monoclonal antibody only specifically recognized human bladder cancer tissue, it showed that the antigen was abnormal glycosylated TFRC, and its epitope Fucα1-4(GlcNAcb1-3)[6OSO3]GlcNAc only was expressed in human bladder cancer tissue cells.

TABLE 2 mass spectrum identification of ABC71 antigen

| Accession | Mass | Score |
| --- | --- | --- |
| TFRC HUMAN | 186395 | 197 |
| Tubulin HUMAN | 36483 | 53 |
| Filaggrin HUMAN | 19176 | 42 |
| Dermcidin HUMAN | 25320 | 35 |
| Actin, cytoplasmic 1 HUMAN | 36127 | 32 |
| Collagen alpha-2 HUMAN | 27329 | 30 |
| Protein NDRG1 HUMAN | 63517 | 30 |
| Tyrosine-protein kinase HUMAN | 35379 | 25 |
| Zinc finger protein 517 HUMAN | 24258 | 20 |
| Stress-70 protein HUMAN | 13576 | 20 |

Embodiment 4

Kit for Detecting Exfoliated Cells in Urine of Human Bladder Cancer:

the ABC71 monoclonal antibody prepared in Embodiment 1 of the present invention was used to couple ABC71 antibody and horseradish peroxidase, so the horseradish peroxidase labelled ABC71 monoclonal antibody (ABC71-HRP) was prepared. Exfoliated cells in urine were collected, and ABC71-HRP was added therein. It was stained by DAB, then was restained by hematoxylin, and was detected under microscope. The kit was suitable for the early screening, prognosis monitoring, and auxiliary pathologic diagnosis of cancer patients. Experiments demonstrate that the kit for detecting exfoliated cells in urine of human bladder cancer had following positive effects compared with the prior art: (1) high sensitivity, since ABC71 monoclonal antibody directly bound to the membrane surface of bladder cancer cells, the HRP coupled to the ABC71 monoclonal antibody catalyzed the development of substrate DAB, the sensitivity of the method was much high than that of the conventional detection methods of exfoliative cytology; (2) strong specificity, since the method used ABC71 monoclonal antibody specifically binding to bladder cancer cells, it is capable of specifically recognizing bladder cancer cells; (3) convenient and rapid, and the cost was low, so the Medical costs of patients were saved. Since the method had the characteristics of a high sensitivity and strong specificity, the detection rate for patients with bladder cancer was high, the waste caused by repeated detections were avoided.

Specific Experimental Method is as Follows:

1) collection of exfoliated cells in urine: the urine of patients with bladder cancer was from Peking University First Hospital.

2) immunocytochemical staining of exfoliated cells in urine: 10 ml fresh urine was taken, 100 ul ABC71-HRP was added therein, and then was incubated at room temperature for 10 minutes. The urine was centrifuged at 1000 rpm for 5 minutes, and the supernatant was discarded. The cells were washed by PBS twice, DAB developing solution was added therein and was developed at room temperature for 10 minutes. The cells were washed by PBS, then was restained by hematoxylin for 30 seconds. The cells were washed by PBS again and then were smeared on a slide for detection under microscope.

3) diagnosis by microscope: The pathological staining result was judged according to the morphological characteristics of bladder cancer cells.

The positive detection rates of the ABC71-HRP method and conventional smear methods were compared, and the result was shown in table 3. The result showed that the urine of 57 patients with bladder cancer from Peking University First Hospital was detected by using ABC71-HRP, wherein the positive detection rate of ABC71-HRP was 91.23% (52/57), which was much higher than that of the conventional exfoliated cell smear (40.35%, 23/57). Therefore, AG-CD71 which is specifically expressed by bladder cancer cells is a bladder cancer marker having strong application prospects, and the monoclonal antibody ABC71 for bladder cancer AG-CD71 can effectively detect tumor cells in urine of patients with bladder cancer.

Although the present invention has been described above in detail through general description and specific embodiments. However, on the basis of the present invention, it would have been obvious to those skilled in the art that some modifications or improvements can be made thereto. Therefore, these modifications or improvements made without departing from the spirit of the present invention all fall within the scope of protection of the present invention.

What is claimed is:

1. An antibody for a human bladder cancer marker AG-CD71, wherein the human bladder cancer marker AG-CD71 is an abnormal glycosylated transferrin receptor, the abnormal glycosylated transferrin receptor is a transferrin receptor (TFRC) carrying a saccharide structure Fucal-4(GlcNAcbl-3)[6OSO3]GlcNAc as an epitope, an amino acid sequence of the abnormal glycosylated transferrin receptor is shown by SEQ ID No: 1; and the abnormal glycosylation is on threonine at position 104 of the abnormal glycosylated transferrin receptor; and the structural formula of the saccharide structure Fucal-4(GlcNAcbl-3)[6OSO3]GlcNAc is:

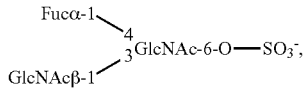

the antibody specifically recognizes the saccharide structure Fucal-4(GlcNAcbl-3)[6OSO3]GlcNAc as the epitope, the antibody is a murine monoclonal antibody ABC71 specific for the human bladder cancer marker AG-CD71, and the murine monoclonal antibody ABC71 is secreted from a hybridoma cell strain with the preservation number CGMCC No. 14312.

2. The antibody according to claim 1, wherein the antibody is applied for preparing a diagnostic reagent of bladder cancer.

3. A conjugate, wherein an antibody ABC71 for the human bladder cancer marker AG-CD71 is conjugated with a substance consisting of a component selected from the group consisting of a biomarker, an antitumor drug, a toxin, a radioactive active agent, and a magnetic particle; and the antibody ABC71 is a monoclonal antibody and is secreted from a hybridoma cell strain with the preservation number CGMCC No. 14312.

4. A kit for detecting or treating human bladder cancer, wherein the kit comprises the antibody according to claim 1.

5. The kit according to claim 4, wherein detecting is performed by immunocytochemistry, and in the immunocytochemistry, the antibody is coupled to horseradish peroxidase to obtain the kit for detecting or treating human bladder cancer.

6. The kit according to claim 4, wherein a detection sample of the kit is human urine containing exfoliated cells of the human bladder cancer.

7. A hybridoma cell strain secreting the monoclonal antibody ABC71 for the human bladder cancer marker AG-CD71 according to claim 1, wherein the hybridoma cell strain is deposited in China General Microbiological Culture Collection Center on 27 Jul. 2017 with a preservation number of CGMCC NO. 14312.

* * * * *

SEQUENCE LISTING

```
<160> NUMBER OF SEQ ID NOS: 1

<210> SEQ ID NO 1
<211> LENGTH: 760
<212> TYPE: PRT
<213> ORGANISM: Homo sapiens

<400> SEQUENCE: 1

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
```

-continued

```
                225                 230                 235                 240
Lys Asp Phe Glu Asp Leu Tyr Thr Pro Val Asn Gly Ser Ile Val Ile
                    245                 250                 255
Val Arg Ala Gly Lys Ile Thr Phe Ala Glu Lys Val Ala Asn Ala Glu
                260                 265                 270
Ser Leu Asn Ala Ile Gly Val Leu Ile Tyr Met Asp Gln Thr Lys Phe
            275                 280                 285
Pro Ile Val Asn Ala Glu Leu Ser Phe Phe Gly His Ala His Leu Gly
        290                 295                 300
Thr Gly Asp Pro Tyr Thr Pro Gly Phe Pro Ser Phe Asn His Thr Gln
305                 310                 315                 320
Phe Pro Pro Ser Arg Ser Ser Gly Leu Pro Asn Ile Pro Val Gln Thr
                325                 330                 335
Ile Ser Arg Ala Ala Glu Lys Leu Phe Gly Asn Met Glu Gly Asp
                340                 345                 350
Cys Pro Ser Asp Trp Lys Thr Asp Ser Thr Cys Arg Met Val Thr Ser
            355                 360                 365
Glu Ser Lys Asn Val Lys Leu Thr Val Ser Asn Val Leu Lys Glu Ile
        370                 375                 380
Lys Ile Leu Asn Ile Phe Gly Val Ile Lys Gly Phe Val Glu Pro Asp
385                 390                 395                 400
His Tyr Val Val Val Gly Ala Gln Arg Asp Ala Trp Gly Pro Gly Ala
                405                 410                 415
Ala Lys Ser Gly Val Gly Thr Ala Leu Leu Leu Lys Leu Ala Gln Met
                420                 425                 430
Phe Ser Asp Met Val Leu Lys Asp Gly Phe Gln Pro Ser Arg Ser Ile
            435                 440                 445
Ile Phe Ala Ser Trp Ser Ala Gly Asp Phe Gly Ser Val Gly Ala Thr
        450                 455                 460
Glu Trp Leu Glu Gly Tyr Leu Ser Ser Leu His Leu Lys Ala Phe Thr
465                 470                 475                 480
Tyr Ile Asn Leu Asp Lys Ala Val Leu Gly Thr Ser Asn Phe Lys Val
                485                 490                 495
Ser Ala Ser Pro Leu Leu Tyr Thr Leu Ile Glu Lys Thr Met Gln Asn
                500                 505                 510
Val Lys His Pro Val Thr Gly Gln Phe Leu Tyr Gln Asp Ser Asn Trp
            515                 520                 525
Ala Ser Lys Val Glu Lys Leu Thr Leu Asp Asn Ala Ala Phe Pro Phe
        530                 535                 540
Leu Ala Tyr Ser Gly Ile Pro Ala Val Ser Phe Cys Phe Cys Glu Asp
545                 550                 555                 560
Thr Asp Tyr Pro Tyr Leu Gly Thr Thr Met Asp Thr Tyr Lys Glu Leu
                565                 570                 575
Ile Glu Arg Ile Pro Glu Leu Asn Lys Val Ala Arg Ala Ala Ala Glu
                580                 585                 590
Val Ala Gly Gln Phe Val Ile Lys Leu Thr His Asp Val Glu Leu Asn
            595                 600                 605
Leu Asp Tyr Glu Arg Tyr Asn Ser Gln Leu Leu Ser Phe Val Arg Asp
        610                 615                 620
Leu Asn Gln Tyr Arg Ala Asp Ile Lys Glu Met Gly Leu Ser Leu Gln
625                 630                 635                 640
Trp Leu Tyr Ser Ala Arg Gly Asp Phe Phe Arg Ala Thr Ser Arg Leu
                645                 650                 655
```

```
Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
        675                 680                 685

Tyr Val Ser Pro Lys Glu Ser Pro Phe Arg His Val Phe Trp Gly Ser
    690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760
```